(12) United States Patent
Poulos

(10) Patent No.: US 10,966,768 B2
(45) Date of Patent: Apr. 6, 2021

(54) METHOD OF INSTALLING SELF-DRILLING, SELF-TAPPING BONE SCREW FOR BICORTICAL PURCHASE

(71) Applicant: Nicholas Poulos, Frontenac, MO (US)

(72) Inventor: Nicholas Poulos, Frontenac, MO (US)

( * ) Notice: Subject to any disclaimer, the term of this patent is extended or adjusted under 35 U.S.C. 154(b) by 0 days.

(21) Appl. No.: 17/070,603

(22) Filed: Oct. 14, 2020

(65) Prior Publication Data

US 2021/0022784 A1 Jan. 28, 2021

Related U.S. Application Data

(60) Continuation of application No. 16/717,924, filed on Dec. 17, 2019, which is a division of application No.
(Continued)

(51) Int. Cl.
| | | |
|---|---|---|
| *A61B 17/86* | (2006.01) | |
| *A61B 17/16* | (2006.01) | |
| *A61B 17/70* | (2006.01) | |
| *A61B 17/84* | (2006.01) | |
| *F16B 25/00* | (2006.01) | |
| *F16B 25/10* | (2006.01) | |

(52) U.S. Cl.
CPC ...... *A61B 17/8635* (2013.01); *A61B 17/1655* (2013.01); *A61B 17/7098* (2013.01);
(Continued)

(58) Field of Classification Search
CPC ... A61B 17/86; A61B 17/8635; A61B 17/864; A61B 17/1655; A61B 17/7098; A61B 17/84; A61B 17/8605; A61B 17/8625; A61B 17/1615; A61B 17/1657; F16B 25/0015; F16B 25/0057; F16B 25/0052;
(Continued)

(56) References Cited

U.S. PATENT DOCUMENTS

| 2,388,482 A | * | 11/1945 | Haynes | ............. | A61B 17/8635 |
| | | | | | 411/387.4 |
| 4,484,570 A | | 11/1984 | Sutter et al. | | |

(Continued)

OTHER PUBLICATIONS

Sutcliffe et al.; Preliminary Experience With the TangoRS; Poryyaxial, Percutaneous, Cement Augmentation Pedicle Screw System; http://www.ispub.om/ostia/index.php?xm1FilePath=jounals/jss/front.xml; 5 pages.

(Continued)

*Primary Examiner* — Marcela I. Shirsat
(74) *Attorney, Agent, or Firm* — Sandberg Phoenix & von Gontard P.C.

(57) ABSTRACT

A self-drilling, self-tapping bone screw is described in which the bone screw has a drill tip free of threads and having a length at least as great as about the thickness of a proximal cortical bone layer, with the drill tip having opposed lands and a helical flute between each of the lands with each of the lands having a cutting edge configured to cut bone as the drill tip is rotated into the bone with the flutes conveying the bone debris away from the drill tip, where a lead thread begins to self-tap internal threads in the proximal cortical bone layer after the drill tip has drilled through the proximal cortical bone layer so as to avoid stripping the threads formed in the bone layer. A method of installation is also disclosed.

9 Claims, 12 Drawing Sheets

Related U.S. Application Data

14/212,246, filed on Mar. 14, 2014, now Pat. No. 10,548,651, application No. 17/070,603, which is a continuation-in-part of application No. 14/148,270, filed on Jan. 6, 2014, now Pat. No. 9,326,801.

(60) Provisional application No. 61/971,287, filed on Mar. 27, 2014.

(52) U.S. Cl.
CPC .......... *A61B 17/1615* (2013.01); *A61B 17/84* (2013.01); *A61B 17/864* (2013.01); *A61B 17/8625* (2013.01); *B23B 2260/124* (2013.01); *F16B 25/00* (2013.01); *F16B 25/0015* (2013.01); *F16B 25/0031* (2013.01); *F16B 25/0052* (2013.01); *F16B 25/0084* (2013.01); *F16B 25/10* (2013.01); *F16B 25/103* (2013.01); *Y10T 29/49963* (2015.01)

(58) Field of Classification Search
CPC ...... F16B 25/00; F16B 25/10; F16B 25/0031; F16B 25/0084; F16B 25/106; F16B 25/103; Y10T 29/49963; B23B 2260/124
USPC ................ 606/301–321, 246–279, 311, 304; 411/411, 412, 413, 395, 426
See application file for complete search history.

(56) References Cited

U.S. PATENT DOCUMENTS

| | | | |
|---|---|---|---|
| 4,537,185 A * | 8/1985 | Stednitz | A61B 17/8635 606/304 |
| 6,048,343 A | 4/2000 | Mathis et al. | |
| 6,517,542 B1 | 2/2003 | Papay et al. | |
| 6,565,572 B2 | 5/2003 | Chappius | |
| 6,755,835 B2 | 6/2004 | Schultheiss et al. | |
| 7,699,852 B2 | 4/2010 | Frankel et al. | |
| 8,747,411 B2 | 6/2014 | Mitchell | |
| 2004/0225292 A1 | 11/2004 | Sasso et al. | |
| 2008/0177335 A1 | 7/2008 | Melkent | |
| 2008/0234756 A1 | 9/2008 | Sutcliffe et al. | |

OTHER PUBLICATIONS

Amendola et al.; Fenstrated Pedicle Screws for Cement-Augmented Purchasein Pateitns With Bone Softening: A Rewivw of 21 Cases; J. Orthopaed Traumatol; (2011) 12: pp. 193-199 DOI 10,1007/s10195-011-0164-9.

Medtronic Introduces the CD Horizon® Fenestrated Screw Spinal System; News Release Jul. 1, 2011; 10:54 AM ET; Memphis, Tenn; p. 1.

Blackburn et al; The Use of Fenestrated Screw System With PMMA Augmentation in Osteoporotic Bone; Department of Neurosurgery, Washington University, St. Louis, MO; pp. 1-8; published before Jan. 6, 2012.

Viper Cortical Fix Fenestrated Screw, Surgical Technique & Product Catalogue, Guide for Open and Mis Procedures; DePuy Spine, Inc. 2011, 9085-38-000: Rev. 2 12/11, www.depuy.com.

Abbott—Surgical Technique Pedestal™ Fenestrated Tap System; The Art & Science of Spine Surgery, Abbott Spine; published before Jan. 6, 2012; pp. 1-19; published before Jan. 6, 2012.

Karmani et al.; The Design and Function of Surgical Drills; Current Orthopaedics. 18. 10.1016/j.cuor.2004.12.011; pp. 484-490.

Saha et al.; Surgical Drilling: Design and Performance of an Improved Drill; Journal of Biomedical Engineering; 1982; vol. 104; pp. 245-252.

* cited by examiner

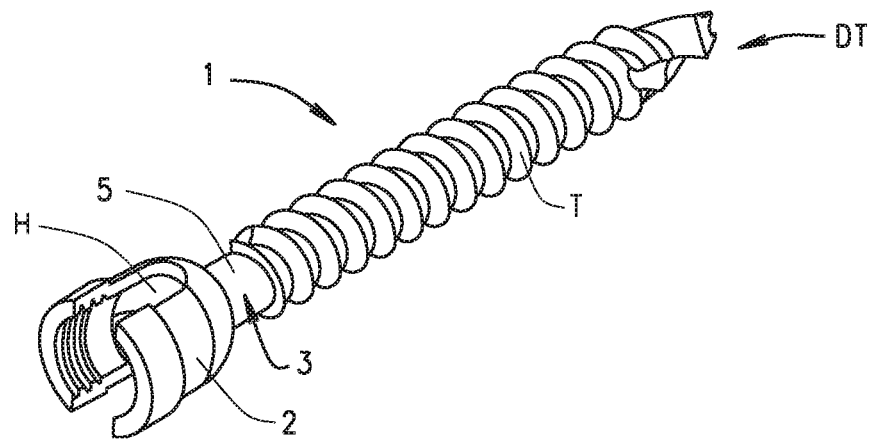
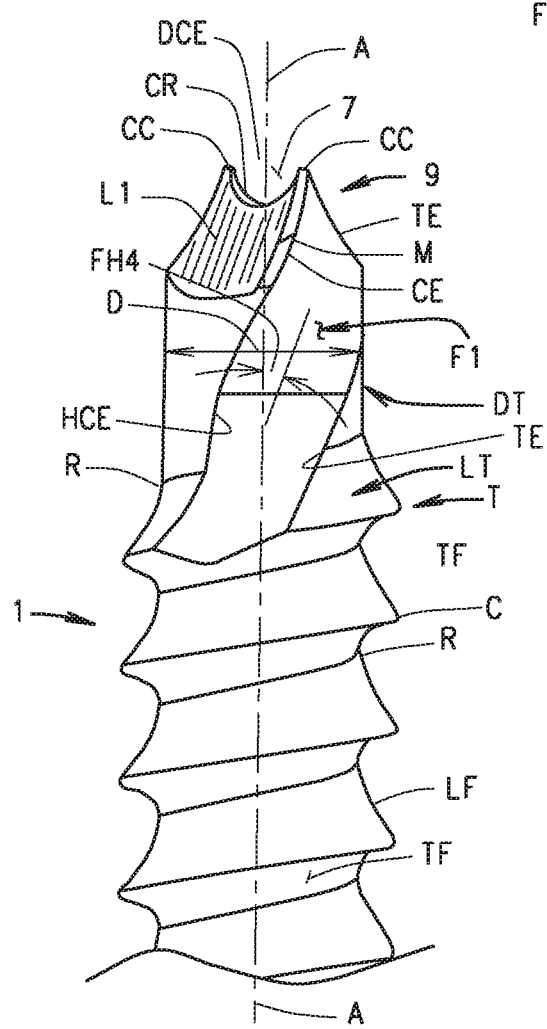
Fig. 2
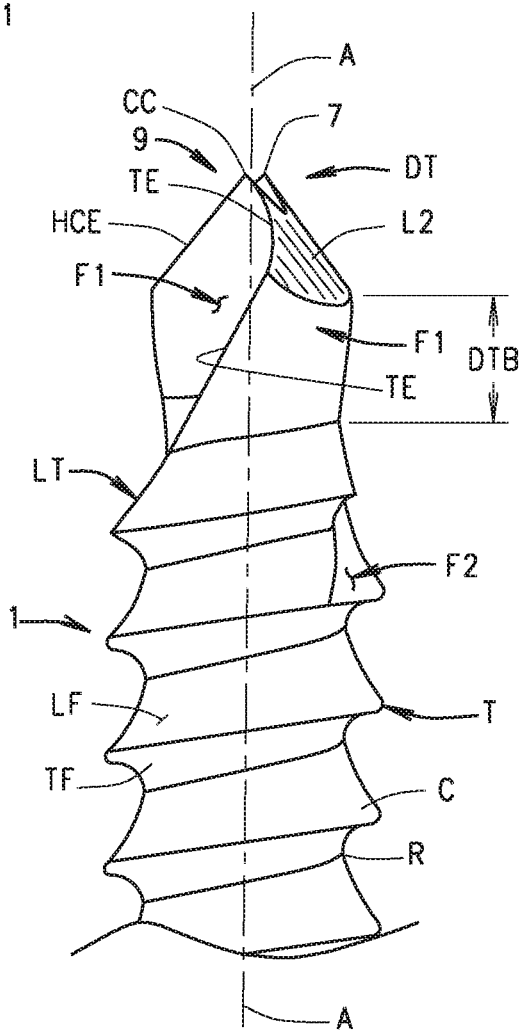
Fig. 3

METHOD OF INSTALLING SELF-DRILLING, SELF-TAPPING BONE SCREW FOR BICORTICAL PURCHASE

CROSS-REFERENCE TO RELATED APPLICATIONS

This application is a continuation of U.S. patent Ser. No. 16/717,924, filed Dec. 17, 2019, which is a divisional of non-provisional U.S. patent application Ser. No. 14/212,246, filed on Mar. 14, 2014, issued as U.S. Pat. No. 10,548,651, which is a continuation-in-part of non-provisional U.S. patent application Ser. No. 14/148,270, filed on Jan. 6, 2014, issued as U.S. Pat. No. 9,326,801, which claims the benefit of U.S. Provisional Application No. 61/791,287, filed Mar. 15, 2013, the entireties of these applications being hereby incorporated by reference and priority hereby being claimed to these applications.

STATEMENT REGARDING FEDERALLY SPONSORED RESEARCH OR DEVELOPMENT

Not Applicable

BACKGROUND OF THE DISCLOSURE

This disclosure relates to a self-drilling and self-tapping bone screw, and in particular to self-drilling, self-tapping, fully cannulated fenestrated and non-fenestrated bone screws, and even more particularly to such self-drilling, self-tapping pedicle screws. This disclosure further relates to methods of installing such bone screws in a variety of surgeries including, but not limited to spine surgery. However, the methods of this disclosure will be described for use with spine surgeries and more specifically in regard to installation of pedicle screws in the sacrum, but those skilled in the art will recognize that the self-drilling, self-tapping bone screws of the present disclosure may be used in a wide variety of applications, including trauma and reconstructive bone surgery. The fenestrated embodiments of the self-drilling, self-tapping bone screws of the present disclosure may be used in conjunction with a method of injecting bone cement into the bone structure into which the bone screw is inserted so as to stabilize the bone structure and to increase the purchase of the bone screw in bone structure having diminished or osteoporotic bone quality, such as described in my U.S. patent application Ser. No. 14/148,207, which is incorporated by reference herein.

Posterior pedicle screws have long been used in spine surgery. Such pedicle screws have been used with rods and other constructs in spine surgery. In cases where the pedicle screws are placed in the sacrum, such constructs have been known to fail distally at the sacrum because the cancellous bone of the sacrum is significantly weaker than lumbar vertebrae body bone. With reference to the sacrum, there is an anterior avascular "safe" zone in the presacral space where major arteries and veins are not present and therefore allow for bicortical or even tricortical purchase of pedicle screws in the sacrum, even where the distal end of the screw extends slightly into this presacral space. However, because in minimally invasive surgical (MIS) techniques the placement of such pedicle screws in the sacrum is typically performed over a guide wire and cannulated pedicle screws are blunt tipped, it is not possible to achieve such bicortical purchase of the screws in the sacrum.

In open techniques to achieve bicortical purchase, the surgeon drills a pilot hole through the entire bone structure before tapping and inserting the bone screw. In percutaneous MIS surgery techniques prior art cannulated pedicle screws are typically blunt tipped, non-self-drilling screws. Additionally a pilot hole cannot be drilled through the distal anterior cortical bone margin without risking the sharp tipped guide wire perforating organs in the pelvis. Consequently a blunt tipped cannulated pedicle screw encountering a distal cortical margin that had not been perforated with a pilot hole would spin in place, not advance, and the threads formed by the self-tapping screw in the more proximal cancellous bone. Consequently the surgeon has to settle for unicortical fixation which is inherently weaker than the bicortical purchase of open techniques.

In open spinal surgical techniques that are intended to achieve bicortical purchase in the sacrum (or other bone structure), the surgeon drills a pilot hole through the entire bone structure, and then taps the pilot hole before inserting the bone screw.

SUMMARY OF THE DISCLOSURE

In accordance with the self-drilling, self-tapping bone screw of the present disclosure may be noted the provision of such a screw in which it is possible using minimally invasive surgical techniques to obtain bicortical purchase of the screw in both the proximal and distal cortical margins of the sacrum without stripping the threads formed by the screw in the more proximal cancellous bone and/or cortical bone.

Still further in accordance with the bone screw of the present disclosure, the self-drilling, self-tapping drill tip of such screw has universal application for all bone screws and such screws are not limited to spine surgery.

In accordance with the self-drilling, self-tapping bone screw of the present disclosure, because such screws avoid a step of tapping threads in the bone structure, the bone screws of the present disclosure increase surgeon's productivity and decreases operating room times for surgeries in which such bone screws are employed.

More specifically, a self-drilling, self-tapping bone screw of the present disclosure is configured to self-drill and to self-thread into bone structure as the screw is installed in the bone structure. The bone structure (e.g., the sacrum) has a proximal (posterior) cortical bone layer or margin at the outer margins thereof to be initially drilled through by the screw, an inner region of cancellous bone, and a distal (anterior) cortical bone layer or margin. The screw comprises a shank having a self-drilling, self-tapping tip at the distal end of the shank with a plurality of substantially uniformly spaced helical bone screw threads along a portion of the shank. The shank has a longitudinal axis extending generally lengthwise of the screw. Each of the threads has a root and a crest, and the spacing of the threads along the shank has a substantially uniform pitch, where the diameter of the roots of the threads constitutes a minor diameter of the threads. Each of the threads is preferably, but not necessarily, a buttress-like thread having a sloped leading flank and a trailing flank more perpendicular to the axis of the screw than the leading flank. The self-drilling tip has a drill tip diameter of about the minor diameter of the threads and is free of threads along its length. Further, the drill tip has a pair of substantially diametrically opposed lands at the distal end of the tip with each of the lands sloping inwardly toward the axis of the screw. The self-drilling tip further has a pair of diametrically opposed helical flutes with one edge of each flute constituting a cutting edge and with the other edge of the flute constituting a trailing edge. Each of the flutes has a pitch substantially greater than the pitch of the threads and has a length such that each the flute intersects at least one of the threads closest to the drilling tip. Each flute has a depth that diminishes along its length such that the depth of the flute distal from the self-drilling tip is only somewhat less than the crest of the thread with which it intersects. The one thread closest to the drilling tip constitutes a lead thread, which is an incomplete thread initially of about the diameter of the drilling tip and where the height of the lead thread gradually increases along its helical length until the lead thread becomes a fully formed thread. This lead thread is configured to form internal threads in the bone structure as the lead thread is rotatably driven into the bone structure. The length of the drilling tip is configured to be at least about the thickness of the proximal cortical bone layer or margin such that the lead thread does not threadably engage the proximate cortical bone layer until the drilling tip has substantially penetrated through the proximate cortical bone layer so as to avoid stripping of the threads formed in the proximal cortical bone margin.

A method of installing a self-drilling, self-tapping bone screw into a bone structure is describe where the bone screw has a cannula extending lengthwise of the screw and having a self-drilling and self-tapping drill tip at its distal end and bone threads along at least a portion of its length. The bone structure into which the screw is to be installed has a proximal and a distal cortical bone layer with a cancellous bone region therebetween. The drill tip has a length approximately equal to or greater than the proximal cortical bone layer, where the thread adjacent the drill tip constitutes a lead thread configured to tap internal threads in the bone structure as the screw is installed in the bone structure. The method of the present disclosure comprises instructing a surgeon to perform the following steps in order to install the screw into bone structure: (a) install a guide wire into a proximal area of the bone structure; (b) pass the cannulated screw along the guide wire until the tip of the screw in close proximity with the bone structure at a desired location for the insertion of the screw; (c) remove the guide wire; and (d) drive the screw into the bone structure by rotating the screw with the drill tip drilling/and or otherwise penetrating substantially through the proximal cortical bone layer before the lead thread begins to form threads in the proximal cortical bone layer.

Other objects and features of the self-drilling, self-tapping bone screws and of the methods herein described will be in part pointed out hereinafter and in part apparent to those skilled in the art.

BRIEF DESCRIPTION OF THE DRAWINGS

FIG. 1 is a three-quarter rear perspective view of a self-drilling, self-tapping pedicle screw of the present disclosure, illustrating a proximal saddle (shown in phantom) carried by the head of the screw for mounting other constructs to the screw;

FIG. 2 is an enlarged scale front elevational view of the distal end of a fully cannulated self-drilling, self-tapping bone screw (e.g., a pedicle screw) of the present disclosure;

FIG. 3 is a right side elevational view of the distal end of the fully cannulated shown in FIG. 2;

FIG. 13 illustrates the placement of a Jamshidi needle into the bone structure of the sacrum, as may be performed in minimally invasive surgery (MIS);

DESCRIPTION OF PREFERRED EMBODIMENTS

Figure 6:
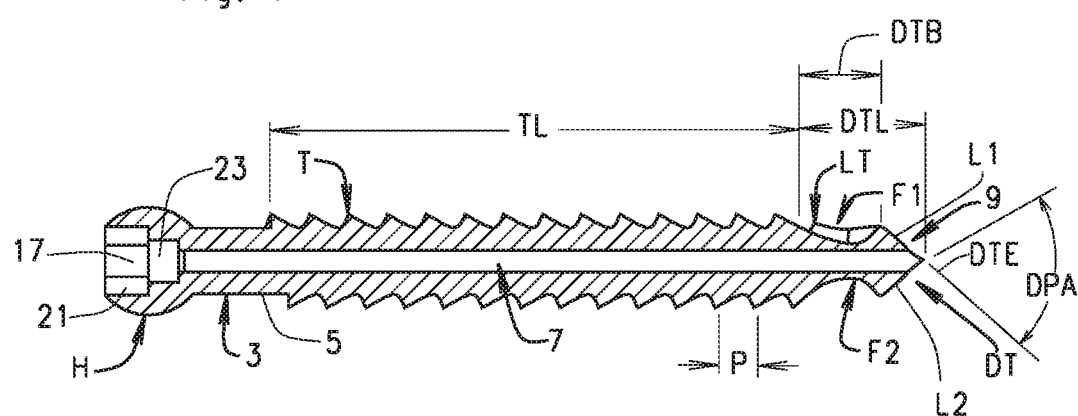
FIG. 6 is a longitudinal cross sectional view of a fully cannulated screw of the present disclosure.
Figure 7:
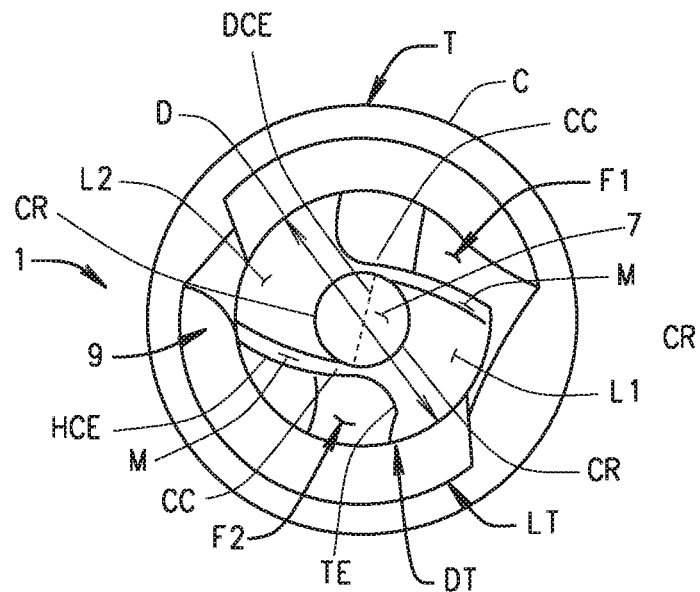
FIG. 7 is a distal end view of the tip or point of the screw shown in FIG. 2.
Figure 8:
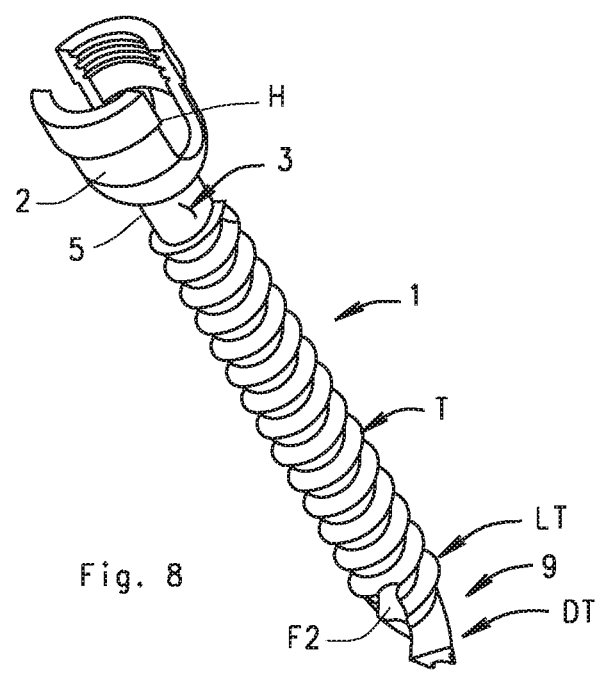
FIG. 8 is another rear perspective view of the screw of the present disclosure with the proximal saddle shown in phantom.
Figure 9:
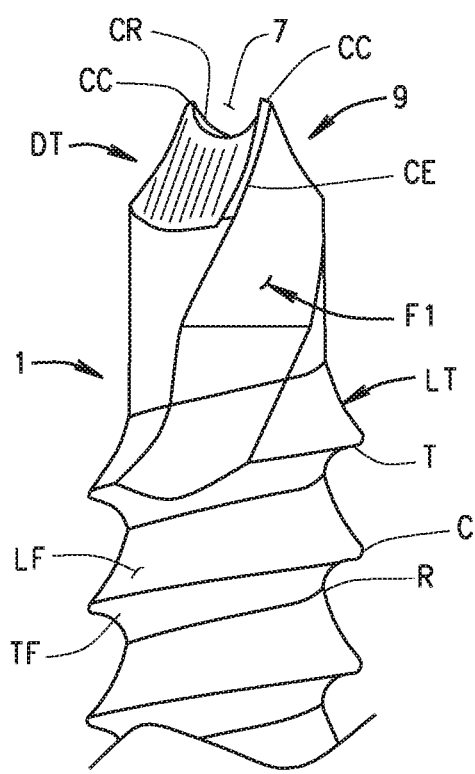
FIG. 9 is a view of the distal end of the screw similar to FIG. 2.
Figure 10:
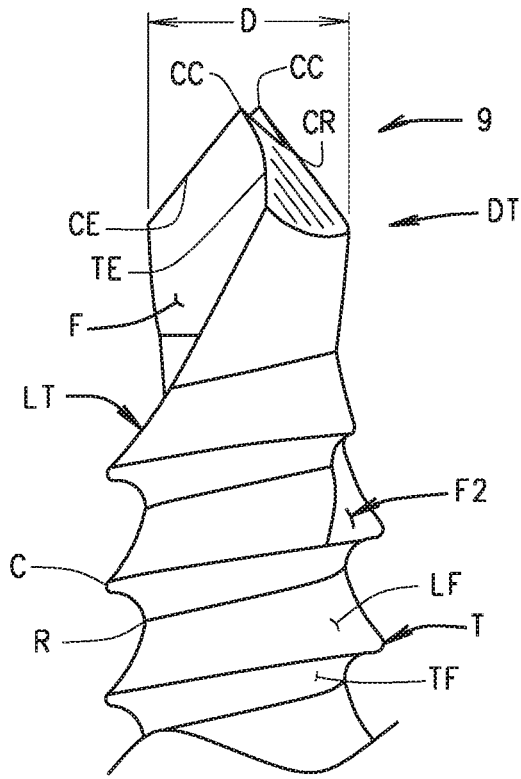
FIG. 10 is a view similar to FIG. 3.
Figure 22:
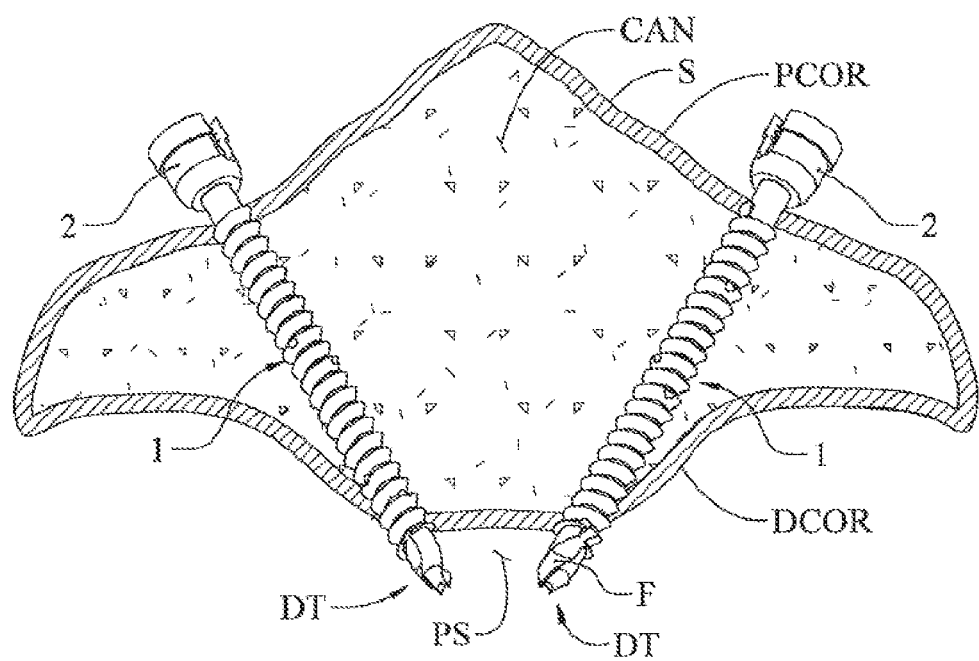
FIG. 22 is a cross sectional view of the sacrum having a pair of self-drilling, self-tapping pedicle screws of the present disclosure placed obliquely in the sacrum where both screws have bicortical placement and purchase in the sacrum and where the distal ends of the screws are in the avascular presacral region of the body.

Referring now to FIG. 1, a self-drilling, self-tapping bone screw, such as a pedicle screw, of the present disclosure is illustrated in its entirety by reference character 1. Screw 1 is a fully cannulated screw that has a part-spherical proximal driving head H for the attachment of a poly-axial saddle 2 (shown in phantom) or other accessory that is conventionally used in spinal surgery. The part-spherical head H allows the saddle 2 or other such appliance to be solidly mounted on the screw, but yet allows the saddle to readily swivel with respect to the screw. Those skilled in the art will recognize that head H and saddle 2 may be of different designs or shapes and may serve different purposes. Screw 1 has a shank, as generally indicated at 3, extending distally from the head. A portion of the shank 3, as indicated by the dimension labeled as thread length TL in FIG. 6, has threads T formed or machined therealong. As indicated at 5, the proximal portion of the shank between the start of the threads and head H is preferably free of threads to allow the saddle 2 or other accessory mounted to the head H to freely swivel on the screw and to not impinge on the threads. As further shown in FIG. 1, the most distal portion of the screw is a self-drilling drill tip, as generally indicated at DT. The threads T and drill tip DT will be described in detail hereinafter. As shown in FIG. 6, a generally cylindric drill tip body DTB extends between the drill tip DT and the distal end of shank 3 and is substantially free of threads, where the overall length of the drill tip DT and the drill tip body DTB is indicated by DTL, and is preferably equal to or somewhat greater than the thickness of the proximal cortical bone layer or margin into which the screw 1 will be inserted so as to prevent stripping of the threads formed in the proximal cortical bone as the drill tip drills through the proximal cortical bone. While the overall length of the drill tip and the drill tip body is sufficient to penetrate the proximal and distal cortical bone margins, it is sufficiently short that it minimizes bicortical screw protrusion into the presacral space PS, as illustrated in FIG. 22.

Figure 11:
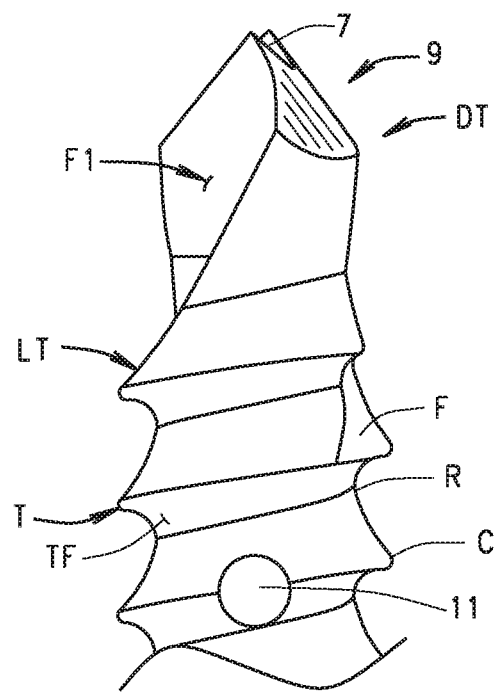
FIG. 11 is a view similar to FIG. 10 illustrating a fenestration in the screw.
Figure 12:
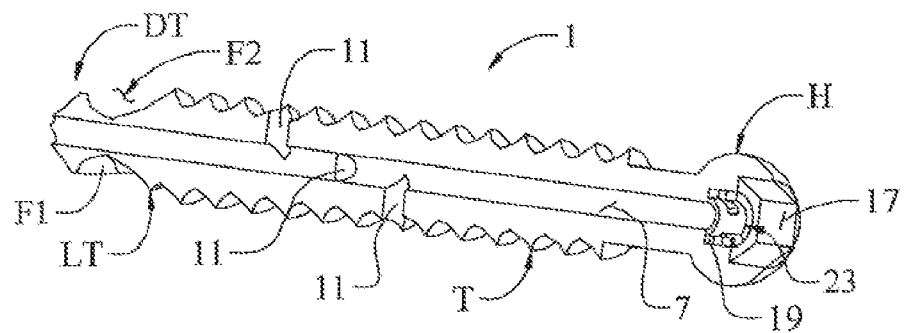
FIG. 12 is a longitudinal cross sectional perspective view of a fully cannulated, self-drilling, self-tapping pedicle screw of the present disclosure having a series of fenestrations along its length where the fenestrations communicate with the central cannula of the screw for the injection of bone cement (or other material) into the surrounding bone structure once the screw has been placed in the bone structure so as to reinforce the bone structure and to increase the purchase and pullout strength of the screw, where this screw has a connector, such as disclosed in my U.S. patent application Ser. No. 14/148,270, filed Jan. 6, 2014, which allows a cement delivery tube and cement pump (not shown herein) to be readily connected to and disconnected from the screw for such injection of bone cement.

More particularly, screw 1, as shown in FIGS. 1-12, is a fully cannulated screw having a cannula 7 (see FIGS. 6 and 12) extending from head H through the distal end of the screw along the screw axis A-A, as shown in FIG. 2. However, those skilled in the art will recognize that the principles of the self-drilling, self-tapping bone screws of the present disclosure may also be incorporated in or used with non-cannulated or solid screws and so-called blind end cannulated bone screws where the cannula 7 does not extend through the tip of the screw. The term "cannula" means any longitudinal bore that extends lengthwise of the screw. As best shown in FIGS. 11 and 12, in another embodiment of the self-drilling, self-tapping bone screw of the present disclosure, a plurality of fenestrations or side bores 11 is provided along the thread length of the screw. These fenestrations preferably, but not necessarily, extend from the crest C of a thread T to the cannula 7. The term "fenestration" means any type of an opening, side bore or aperture leading from the cannula to the exterior of the screw. It will be appreciated that the number of fenestrations can vary, depending on the application for the screw. For example, 3-6 fenestrations may be provided in a typical blind end cannulated pedicle bone screw of the present disclosure that is to be employed for placement in the sacrum. Preferably, but not necessarily, the fenestrations 11 are located in the middle third of the thread length TL of the screw so that the cement injected into the surrounding bone structure is injected primarily into the cancellous bone of the sacrum. FIG. 11 illustrates a fully cannulated screw 1 having its cannula 7 extending from head H through the tip 9 of the screw. The fenestrations may be located at different positions along the length of the screw and at different radial positions around the shank of the screw so that bone cement may be substantially uniformly injected into surrounding bone structure in proximity to the fenestrations, such as described in my aforementioned U.S. patent application Ser. No. 14/148,270. The diameter of the cannula 7 is preferably about 1.6 mm. and the diameter of the fenestrations may be about 1.6 mm. The 1.6 mm. cannula in the screws shown in FIGS. 2-11 results in a screw having sufficient strength intended for such bone screws, and such that the strength of such screws is not unduly compromised. As will be understood by those skilled in the art, such injection of bone cement into the bone structure surrounding the length of screw 1 is used to reinforce the bone and to enhance purchase and pullout strength of the screw in the bone structure, particularly in weaker cancellous bone. However, those skilled in the art will understand that within the broader applications of the bone screw of this disclosure, such fenestrations 11 and injection of bone cement may not be required or desired. It will be also understood that the diameter, spacing and location of the fenestrations 11 and the diameter of the cannula 7 may vary depending on the application of the screw and the cement that is to be injected into the surrounding bone structure.

Referring now to FIGS. 1-12, the self-drilling, self-tapping bone screw 1 of the present disclosure will be described in greater detail. As mentioned, screw 1 has a self-drilling drill tip DT at its distal end. It will be understood that the provision of this self-drilling drill tip allows the screw of the present disclosure to be placed in bone structure without the pilot hole through the entirety of the bone structure including the distal cortical margin. The screw of the present disclosure will simultaneously form a hole through the bone and form threads for securing the screw in the bone structure as the screw is screwed into the bone structure. No tapping is required.

Before describing the drill tip DT in detail, a more complete description of the threads T will be provided. As previously described, screw 1 has bone threads T formed along the thread length TL of shank 3, as shown in FIG. 6. Threads T are preferably, but not necessarily, external buttress-like threads. As best shown in FIGS. 2-5 and 9-11, each thread T has leading flank or face LF and a trailing flank or face TF. Preferably, the thread crest C has a sharp edge formed by the intersection of the leading and trailing flanks LF and TF of the thread so as to maximize the thread height (the distance from the root R of the thread to the thread crest C). By maximizing the height of the threads T, thread purchase in bone structure and pullout strength is maximized. It will be appreciated that the sharp edge of the thread crest C may have a small flat outer surface generally parallel to the thread axis A-A of the screw or may have a slight radius. For example, the thread crest C may have a width of about 0.15 mm.

As shown in FIGS. 2-5, and 9-11, the leading flank LF of each thread T is shown to be somewhat curved or slanted. The slanted leading flank LF allows the external treads of the screw 1 to form the corresponding internal threads in the bone structure with a relatively low force required to drive or rotate the screw into the bone structure so as to self-drill and self-tap the threads in the bone structure. In contrast, the trailing flank TF is more perpendicular to the axis AA of the screw, which increases the purchase of the screw in the bone structure and results in improved pullout strength of the screw.

Referring now to FIGS. 2-5 and 9-11, the drill tip or point DT of the screw 1 will be described in greater detail. As shown in FIG. 2, the drill tip DT has a diameter D, which may be approximately the same as the minor diameter of threads T. This facilitates manufacture of the screw and facilitates penetration of the screw tip into cortical bone. For example, this drill point diameter D may be about 4.6 mm., but other drill point diameters both smaller and larger may be satisfactory. Still further, the outer diameter of threads T is may be about 6.5 mm., and the root diameter of the threads may be about 4.6 mm. However, in accordance with screw of the present disclosure, these diameters may vary considerably. However, if the screw 1 is a cannulated screw, the root diameter should not be appreciably smaller than about 4.6 mm. because the screw with the cannula may not have sufficient strength.

For example, threads T may have a pitch P, as shown in FIG. 6, of about 2.7 mm. and the fully formed complete threads may have a thread depth or height of about 0.95 mm. from the root R to the crest C of the thread. The pitch of a thread T is the uniform spacing between corresponding points on adjacent threads forms in the same axial plane and on the same side of the axis A-A. It will be understood that these dimensions and characteristics of the threads are only exemplary or preferred and that these thread dimensions and characteristics may vary considerably.

As heretofore described, the screw 1 shown in FIGS. 2-12 is a fully cannulated screw having a cannula 7 extending from head H through the distal end of the screw. As perhaps best shown in FIGS. 2-5, 7, and 9-11, the drill tip or point DT has two generally opposed planar drill point lands, as indicated at L1 and L2, located on opposite sides of the drill point. These lands converge toward the longitudinal axis of A-A of the screw and form a sharp distal cutting edge DCE at the distal end of the screw and form a drill point angle DPA, as shown in FIG. 6. In accordance with the present disclosure, a drill point angle DPA of about 70°, plus or minus about 5°, is preferred, but is not required, because it has been found that such a drill point angle facilitates penetration of the drill point into bone structure with a relatively low axial force applied to the screw so that the screw will penetrate the bone structure with minimal insertion force or torque. Other drill point angles ranging between about 90° and about 118° were tried, but these other drill point angles did not result in the desired aggressive cortical bone penetration and low insertion torque attributes of a drill point having a drill point angle of about 70°, plus or minus about 10°. This preferred drill point angle results in a lower axial force that is needed to initially penetrate the tip of the screw into the bone structure (as compared with greater drill point angles greater than about 90°), and it lessens the torque required to rotate the screw as it self-drills into the bone structure.

Figure 4:
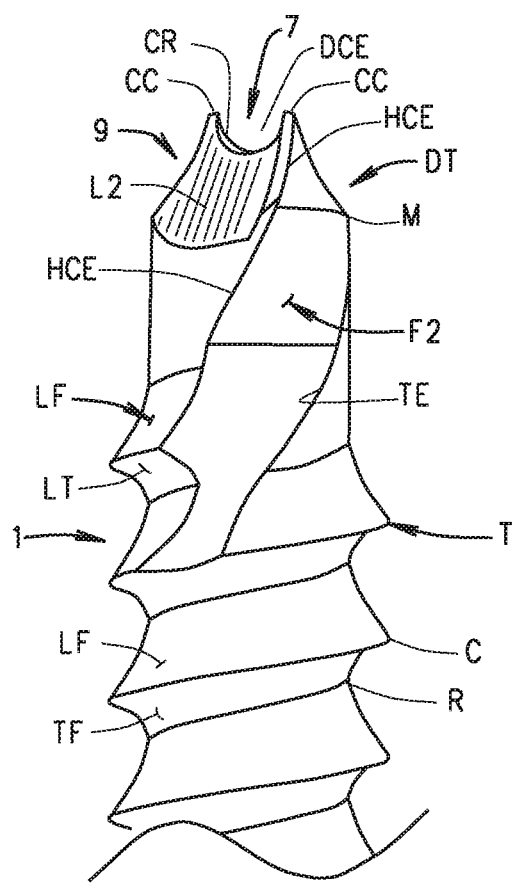
FIG. 4 is a rear elevational view of the distal end of the screw shown in FIG. 2.
Figure 5:
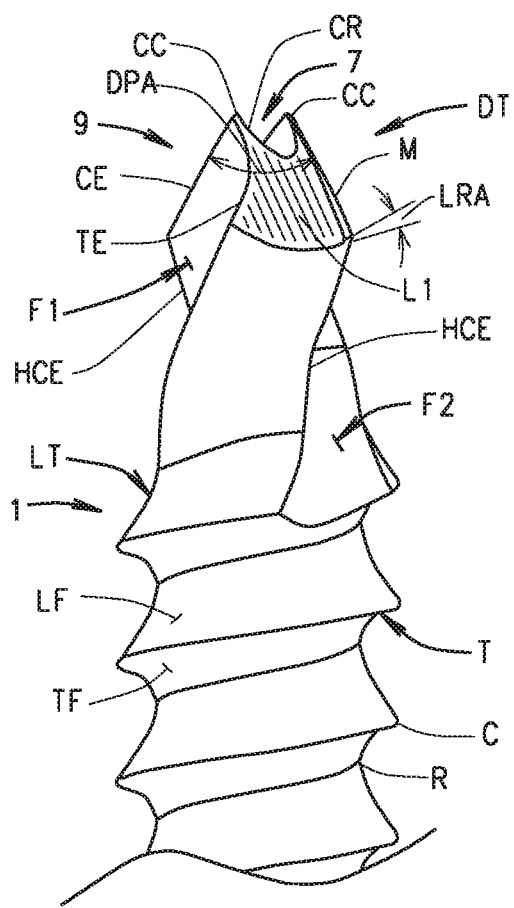
FIG. 5 is a left side elevational view of the other side of the distal end of the screw shown in FIG. 2.

As indicated at F1 and F2, a pair of generally helical flutes is formed on opposite sides of the drill point between lands L1 and L2. These helical flutes extend from the distal end of the drill tip DT toward the proximal end of the screw and have a pitch of about 14 mm, which is substantially greater than the pitch P of the threads T. Because of this relatively large pitch, the flutes F1 and F2 have a helix angle FHA (as shown in FIGS. 2 and 3) substantially less than the helix angle of the threads T and thus each of the flutes extends lengthwise along the drill tip DT, along the drill tip body DTB, and through at least the first thread T (as is the case for flute F1) or partially into the second thread (as is the case for flute F2). It will be understood that the helix angle of the flutes and of the threads T is a function of their respective pitches—the smaller the pitch the greater the helix angle. As shown in FIG. 2, the flutes F1 and F2 have a margin M extending generally from its respective core cutting tip CC along the leading edge of its respective lands L1 or L2. The conical outer surface of margin M is preferably slightly raised above the conical surface of its respective land L1 or L2, to reduce friction as the screw is inserted into bone structure. The leading edge of the margin forms a helical cutting edge or lip HCE. Each of the helical cutting edges HCE is at a slight angle (e.g., preferably about 2°-10°, and more preferably about 3°, plus about 3° minus about 1°) relative to its adjoining wall of its adjacent flute F1 or F2 with this last-mentioned angle constituting a rake angle for enhancing the cutting action of cutting edge HCE as the drill tip DT is fed into bone structure. At the proximal end of each of the margins M, an angle is formed between a line tangent to the periphery of the distal end of its respective land L1 or L2 and a plane perpendicular to the axis A-A of the screw referred to as a "Lip Relief Angle" LRA. This angle LRA is shown in FIG. 5. Lip relief angles of 15° vs 20° vs 25° were tried in cadaver tests and it was determined that a lip relief angle of about 25° was the most favored because it maximized cortical bone penetration and minimized insertion torque.

The intersections of the lands L1 and L2 with the distal end of cannula 7 form core cutting tips CC, which are the most distal and prominent portion of a thin walled cutting rim CR, that form a bone core (not shown) as the self-drilling drill tip bores into the bone structure. The cutting rim CR has, for example, a diameter of about the same as cannula 7 (about 1.6 mm.) such that it forms a bone core of somewhat a smaller diameter (e.g., about 1.5 mm.) that is received within the cannula as the screw is advanced into the bone structure. Those skilled in the art will appreciate that the open cannula 7 and the core cutting tips CC and cutting rim CR eliminate a chisel edge that would normally be present on a solid drill tip. It will be appreciated that such chisel edges offer substantial resistance to penetration of a solid drill point into a substance. Further, the core cutting tips CC and cutting rim CR allow the tip of the screw 1 to more readily penetrate into the bone structure and to form the bone core with less axial force applied to the screw to advance the screw into the bone material than would be required if a solid drill point for screw 1 were employed. This lessens the axial force needed for the drill tip DT of screw 1 to initially penetrate the bone, and, more particularly, to penetrate the harder cortical bone.

As shown in FIG. 2 and as mentioned above, threads T are, for example, right-hand threads so that as screw 1 is rotated in clockwise direction and as an axial load is applied to the screw, the screw will be driven into the bone structure. Thus, as the screw 1 initially penetrates into the bone structure, the core cutting tips CC, cutting rim CR and cutting edge CE cut into the bone forming the aforementioned bone core (not shown) that is received in cannula 7 and form bone cutting debris or chips. Such bone debris or chips formed by the cutting edges CE of the drill tip DT flow along the flutes F1 and F2 away from the tip of the screw toward the threads. As the bone chips or debris reach the proximal ends of the flutes, the depth of the flutes decreases, as perhaps best shown in FIGS. 4 and 5, such that the bone chips or debris (including both cortical and cancellous bone chips) are compacted or compressed into the surrounding bone structure (and particularly into the surrounding cancellous bone) near the proximal ends of the flutes as the screw is inserted into the bone structure thus strengthening the surrounding bone structure, and enhancing thread purchase and the pullout strength of the screw 1.

As previously mentioned, as a fully cannulated screw 1 is rotated in clockwise direction, after the drill tip DT has drilled through the proximal cortical bone layer, the most distal or lead thread LT, as shown in FIGS. 2-12, forms a corresponding internal helical thread in the bone structure. In general, a lead thread is an incomplete thread that is fully formed at its root R but is not fully formed at its crest C. The height of the lead thread gradually increases along its helical length until the lead thread becomes a fully formed complete thread. This lead thread LT self-taps the internal threads in the bone structure as the screw 1 is advanced into the bone structure with a minimal amount of torque required to install the self-drilling, self-tapping screw 1 of the present disclosure into bone structure.

Figure 18:
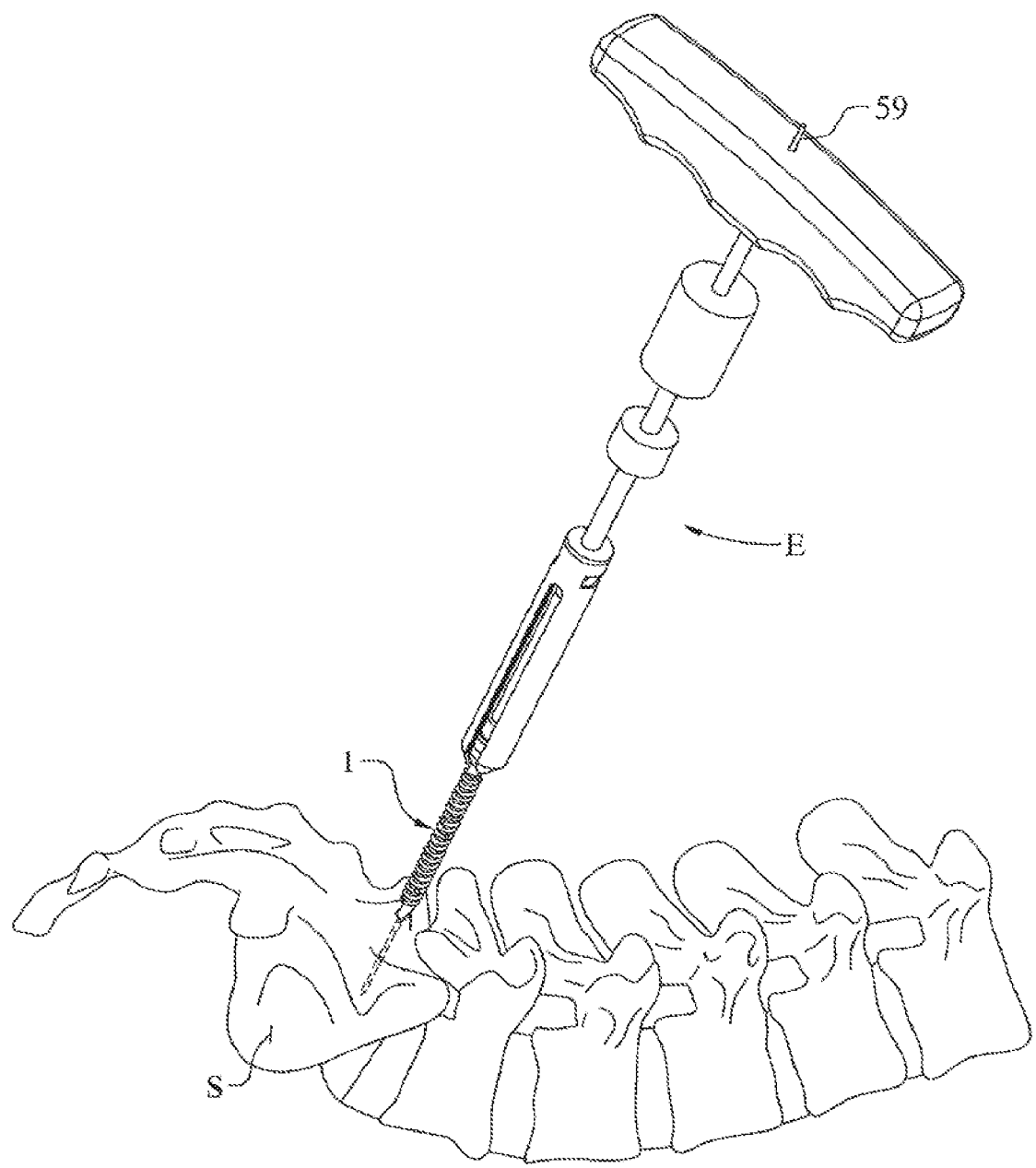
FIG. 18 illustrates the initial placement of a self-drilling pedicle screw of the present disclosure using a screw extender.
Figure 19:
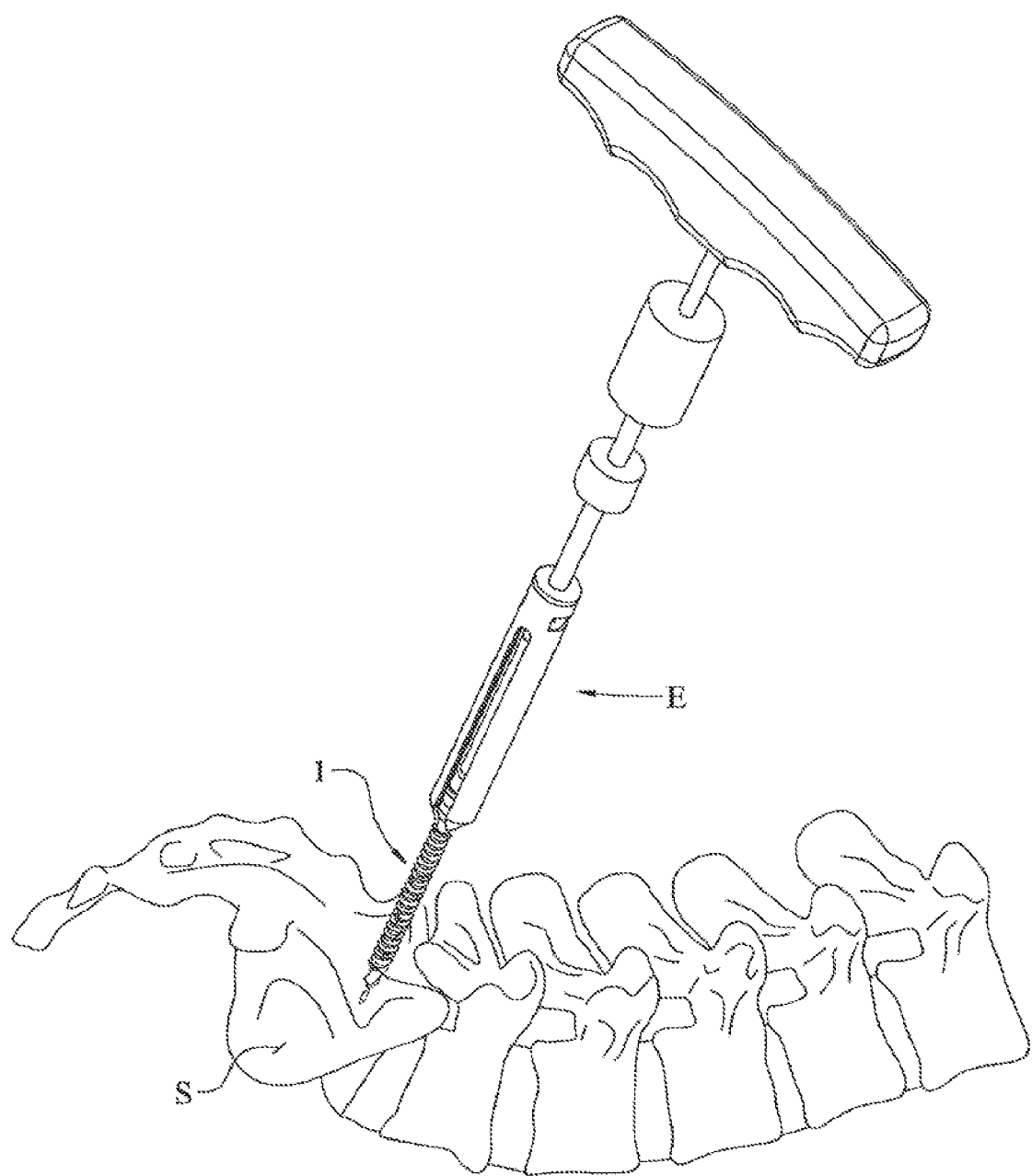
FIG. 19 illustrates the final positioning of a self-drilling, self-tapping pedicle screw of the present disclosure in the sacrum using the aforementioned screw extender.
Figure 20:
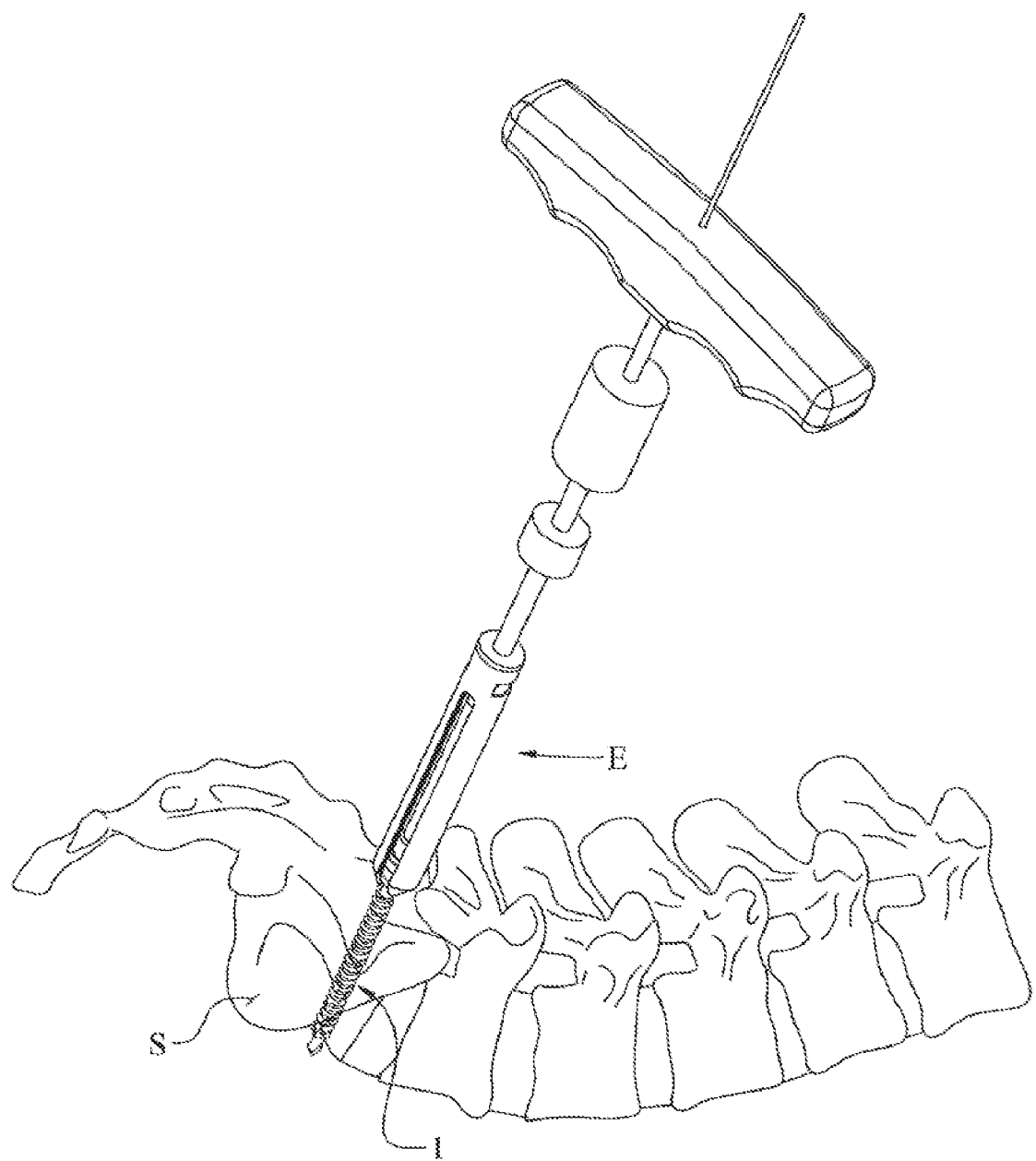
FIG. 20 illustrates the final positioning and insertion of a self-drilling, self-tapping pedicle screw of the present disclosure achieving bicortical purchase in the sacrum.
Figure 21:
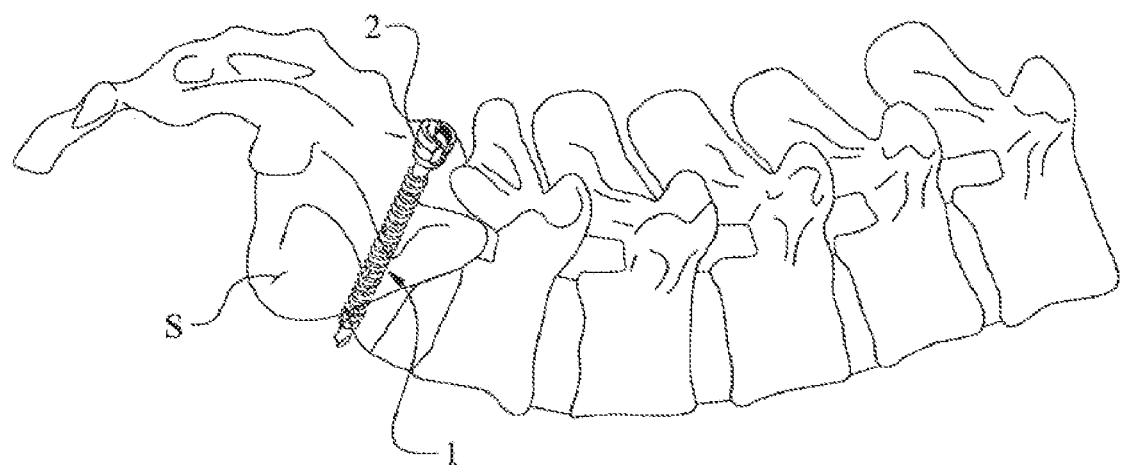
FIG. 21 is a view similar to FIG. 20 with the screw extender removed.

As best shown in FIG. 12, screw head H has an internal driving socket, as generally indicated at 17, formed therein such that the socket is coaxial with the longitudinal axis of the screw. Socket 17 is shaped to receive a complimentary screw driving tool (e.g., a screw driver such as indicated at 65, as shown in FIG. 18 of my co-pending U.S. patent application Ser. No. 14/148,270). The screw-driving socket 17 is shown in FIG. 12 to be in the shape of a hexagonal socket for receiving a hexagonal screw-driving tool, but those skilled in the art will understand that any shape screw-driving socket, such as a star-shaped or a Torx socket, may be employed. The reference characters 17 and greater correspond to the reference characters used in the aforesaid U.S. patent application Ser. No. 14/148,270.

As further shown in FIG. 12, a female bayonet connector or collar, as generally indicated at 23, may be installed within an inner cylindrical inner bore 19 of the screw head H. Connector 23 is more fully described in my co-pending U.S. patent application Ser. No. 14/148,270, which is incorporated by reference in its entirety herein.

Referring now to FIGS. 13-23, surgical procedures or methods in accord with the present disclosure are shown. Such surgical procedures are for the installation of the self-drilling bone screws 1 of the present disclosure is illustrated in percutaneous minimally invasive surgery (MIS). It will be understood that these screws can also be used in open spine surgeries.

Figure 13:
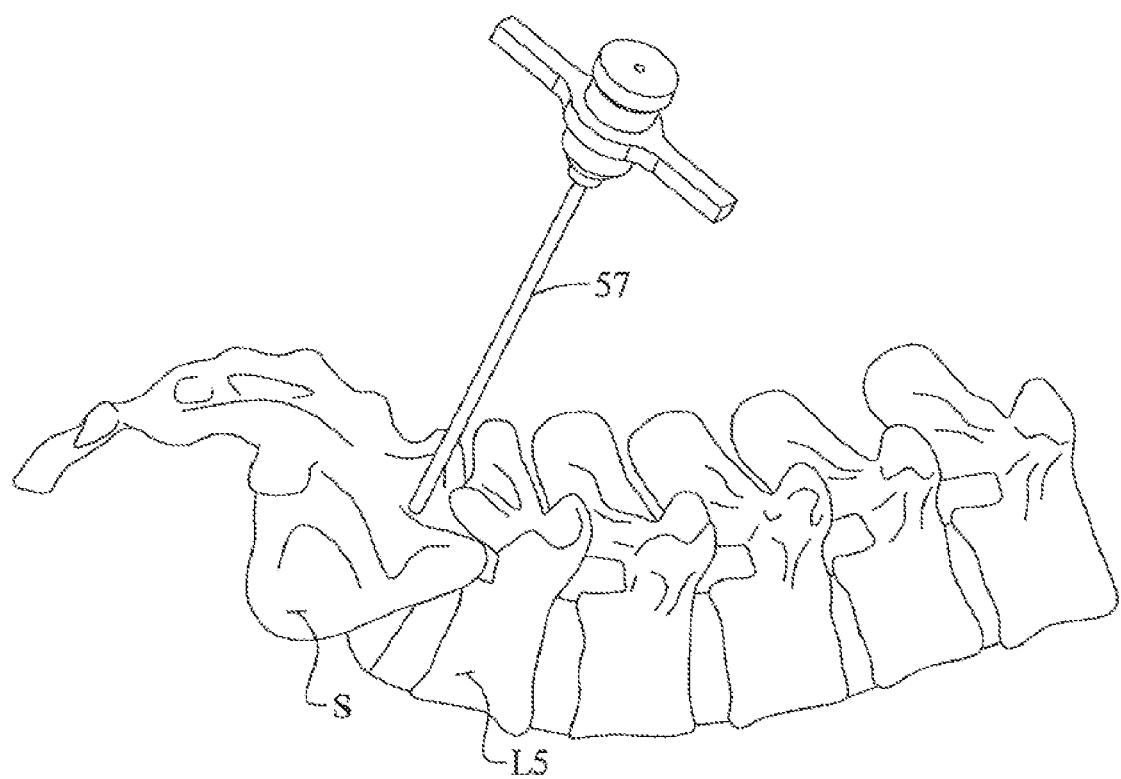
FIG. 13 is a perspective view of a surgical procedure or method of the present disclosure illustrating the installation of a self-drilling, self-tapping bone screw of the present disclosure in the sacrum for bi-cortical purchase of the screw in the sacrum, where
Figure 14:
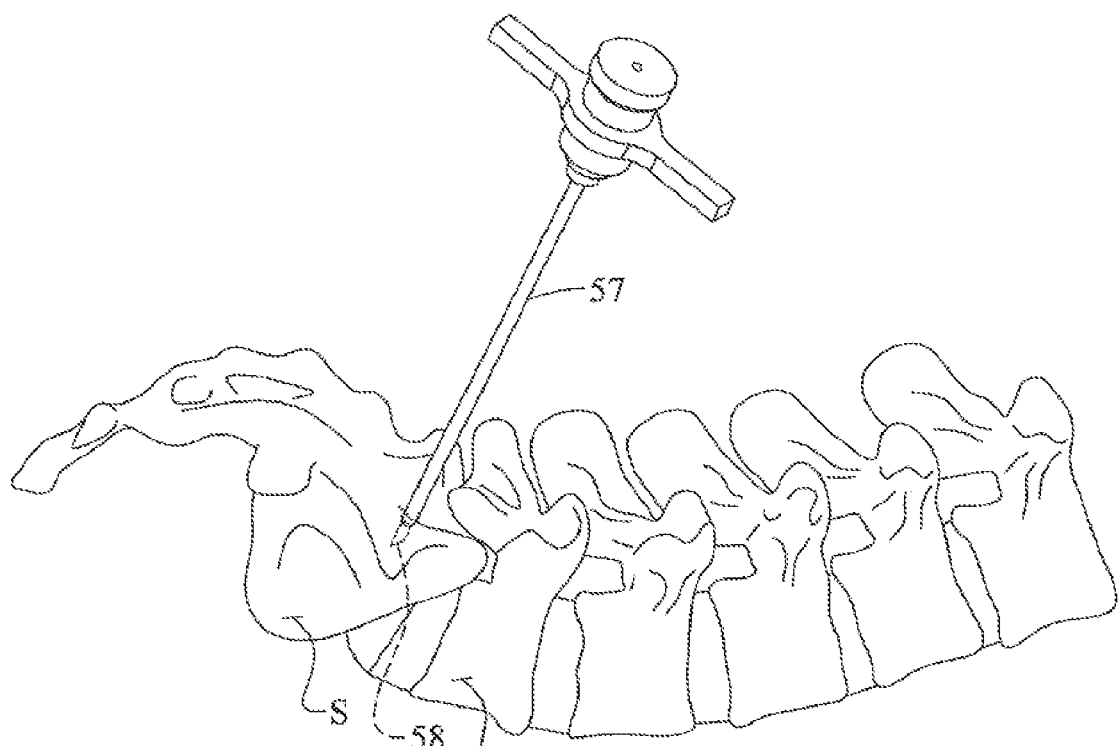
FIG. 14 further illustrates the insertion of the Jamshidi needle and trocar into the sacrum.
Figure 15:
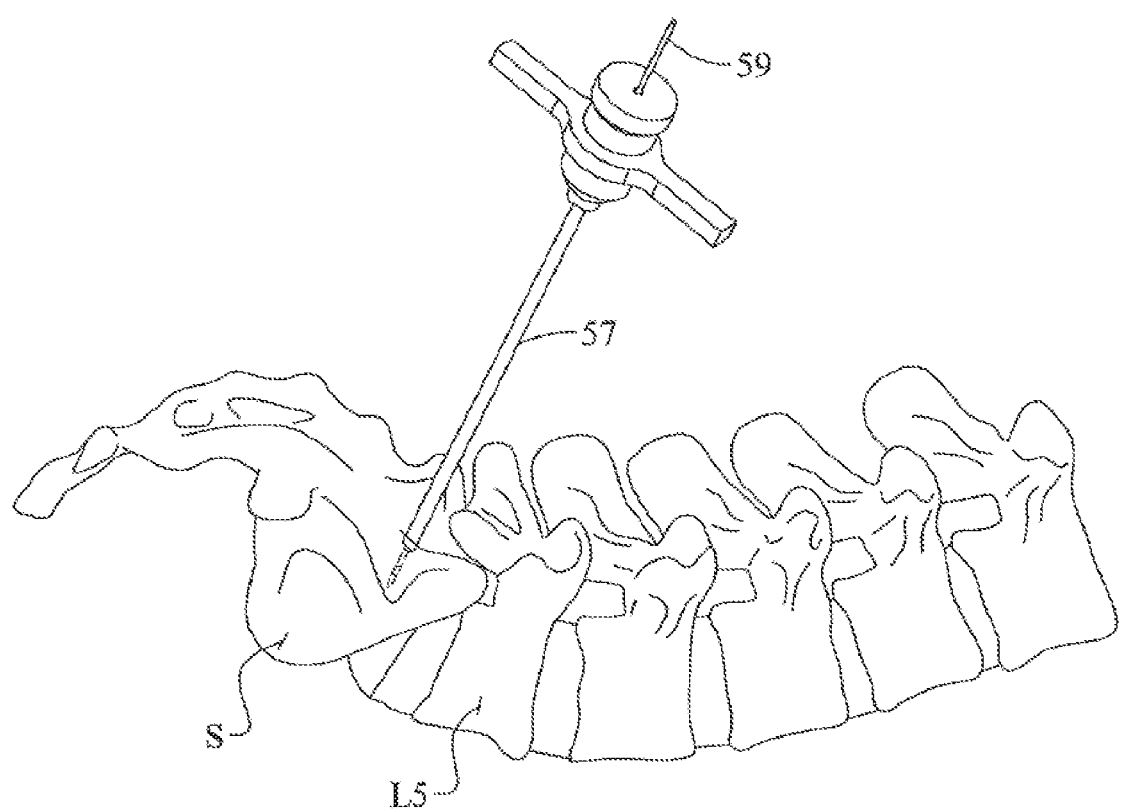
FIG. 15 illustrates the insertion of a sharp guide wire through the Jamshidi needle into the sacrum.

As shown in FIGS. 13 and 14, after a posterior percutaneous incision (not shown) is made proximate the desired location of the self-drilling bone screw 1 to be installed, a Jamshidi needle 57 is inserted into the incision until it contacts the surface of the bone structure, such as the sacrum S, and is forced into the bone structure of the sacrum. Such Jamshidi needles and trocars are well known to spine surgeons, and they typically include an outer hollow needle and a trocar 58, which is forced a short distance (e.g., 10-15 mm. or so) into the posterior of the sacrum. This is preferably done under fluoroscopic visualization to insure proper location of the Jamshidi needle and the trocar. As shown in FIG. 15, after the trocar 58 is removed, a sharp guide wire 59 is inserted through the Jamshidi needle 57 so as to penetrate a relatively short distance into the posterior of the sacrum (or other bone structure) in the conventional manner. The guide wire 59 serves to locate the insertion point for the screw and to establish a reference line along which the screw 1 is to be installed in the bone structure so that the screw is properly positioned and oriented relative to the sacrum or other bone structure for installation along a desired line of insertion or trajectory.

Figure 16:
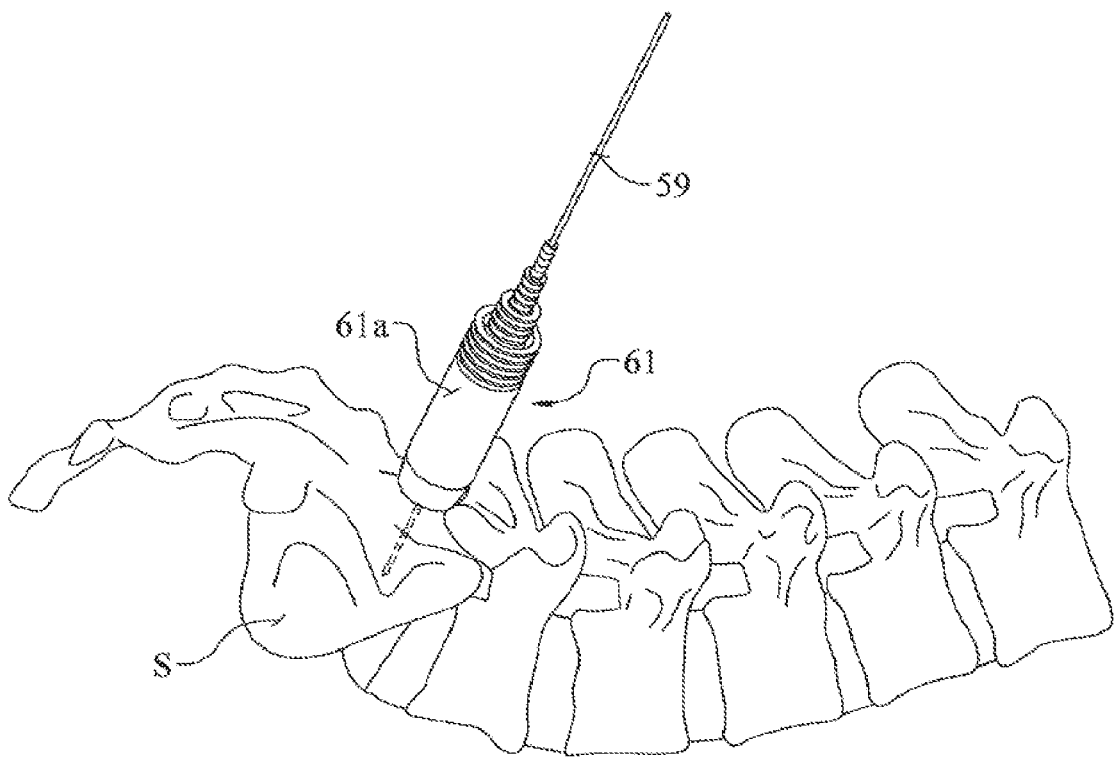
FIG. 16 illustrates the placement of sequential dilation tubes over the guide wire for the dilation of fascia and muscle for bicortical placement of a screw of the present disclosure in the sacrum, where the fascia and muscle are not shown for purposes of clarity.
Figure 17:
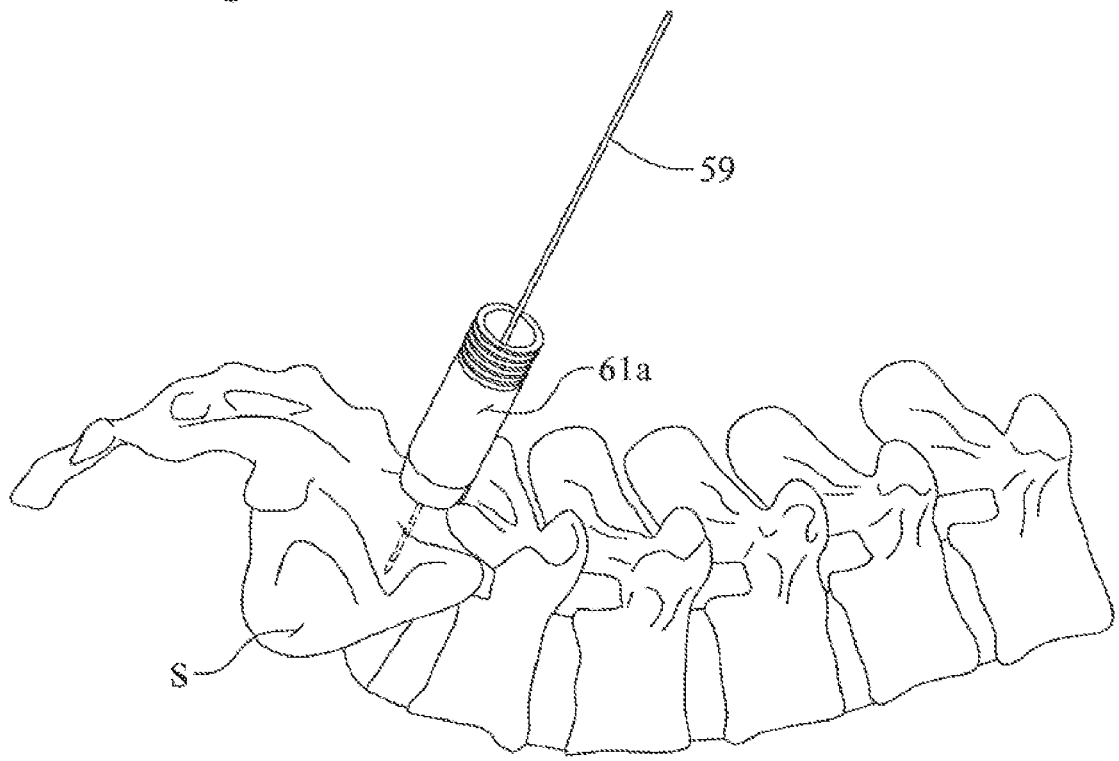
FIG. 17 illustrates the establishment of a minimally invasive surgical corridor through the largest diameter dilator, as shown in FIG. 16.

As shown in FIG. 16, sequential dilation tubes, as generally indicated at 61, are installed over the guide wire 59 in the conventional manner so as to adequately dilate the fascia and muscle (not shown) surrounding the incision thereby to provide a MIS surgical corridor. As shown in FIG. 17, the smaller diameter dilation tubes 61 are removed and the largest diameter tube 61a remains in place to form a surgical corridor.

The placement and insertion of a self-drilling, self-tapping pedicle screw 1 of the present disclosure in the sacrum is shown in FIGS. 18-22. The length of the screw 1 to be inserted may be determined by the surgeon upon fluoroscopic examination of the bone structure into which the screw is to be inserted as well as by reviewing of preoperative imaging. As shown in FIG. 18, a fully cannulated screw 1 of the present disclosure has a tubular screw extender E attached to the head H of the screw. Such a screw extender may be a commercially available extender, such as is commercially available from Medtronic, Inc. of Minneapolis, Minn., used in conjunction with Medtronic's CD Horizon® Sextant II® system. The screw and the screw extender are passed over guide wire 59 until the tip of the screw is nearly in engagement with the bone structure of sacrum S. The guide wire establishes the desired position and orientation of the screw so that it may be installed along a desired line of insertion or trajectory. The surgeon then begins to rotate the screw via the handle of the extender E so that the drill tip DT of screw 1 begins to penetrate the proximal cortical layer PCOR (See FIG. 22). After the screw has penetrated a short distance, the surgeon removes the guide wire so as to avoid binding. It will be appreciated that upon removal of the guide wire 59, because the screw has been started into the bone structure, the guide wire has insured that the screw is started at the correct point on the bone structure and that the screw is correctly aligned with its desired trajectory. The surgeon then continues to turn the handle of the screw extender E in clockwise direction to install the screw 1 such that the screw self-drills into the bone structure and self-taps the internal threads in the bone structure.

As shown in FIGS. 3 and 6, the length of the drill tip body (DTB) preferably is substantially equal to or somewhat greater than the thickness of the proximal and distal cortical bone layers or margins into which the screw is to be inserted. As shown in FIG. 22, for example, the sacrum S has an outer or proximal margin or layer of cortical bone, as indicated at PCOR, and an inner region of cancellous bone, as indicated at CAN, and a distal margin or layer of cortical bone, as indicated at DCOR. It will be appreciated that it may take several revolutions of the screw 1 for the drill tip DT to drill or to otherwise penetrate through the proximal cortical bone layer PCOR. It will be understood that a pilot hole (not shown) made in the proximate cortical bone layer PCOR by the trocar 58 and guide wire 59 aids in starting the drill tip DT to penetrate the cortical bone. With the length of the drill tip body DTB being equal to or somewhat greater than the thickness of the proximal cortical bone structure PCOR, the lead thread LT on screw 1 will only engage the proximal cortical bone after the drill tip has penetrated through the proximal cortical bone. In this manner, the lead thread LT will not begin to self-tap internal threads in the proximal cortical bone until the drill tip DT can more readily self-drill (penetrate) into the softer cancellous bone of the sacrum S. As the internal threads are formed in the proximal cortical bone and then in the cancellous bone, the screw 1 will axially advance into the bone structure at the rate of the pitch of the threads. In other words, if the pitch of threads T is about 2.7 mm., for each turn of the screw, the screw will advance axially into the sacrum about 2.7 mm. As noted, the length of the drill tip body DTB is preferably somewhat longer than the thickness of the proximal cortical bone layer PCOR. This insures that the threads are not formed in the proximal cortical bone until the drill tip is able to more readily penetrate the cancellous bone, which, in turn, prevents the threads formed in the proximal cortical bone from being stripped because the drill tip cannot advance through the cancellous bone at the rate the drill bit is advanced by the threads formed in the proximal cortical bone.

As the surgeon continues to rotate the handle of the extender E and screw 1 in clockwise direction, the screw will continue to penetrate into the cancellous region CAN and the screw will self-tap threads in the proximal cortical bone PCOR and in the cancellous bone. When the drill tip DT comes into contact with the distal cortical bone layer or margin DCOR of the sacrum, the threads formed by the self-tapping screw 1 in the proximal cortical bone and in the cancellous bone have sufficient strength such that these threads and the continued rotation of the screw will apply a sufficient axial force to the drill tip such that the drill tip will self-drill or otherwise penetrate through the distal cortical bone at the rate of axial advancement of the screw due to pitch of threads T engaging the matching threads in the bone structure. As the lead thread LT comes into engagement with the distal cortical bone layer DCOR, the lead thread and the other threads on screw 1 will self-tap thread in the distal cortical bone without stripping the threads formed in the proximal cortical bone layer or in the cancellous bone of the sacrum. In this manner, bicortical purchase of the self-drilling, self-tapping screw 1 of the present disclosure is achieved. The length of the screw 1 is selected so that it will advance only a few millimeters into the avascular presacral space PS, as shown in FIG. 22 with threads T of screw 1 engaging the proximal cortical bone margin or layer COR, the inner cancellous bone CAN, and the distal cortical margin COR for maximum pullout strength and fixation.

Figure 23:
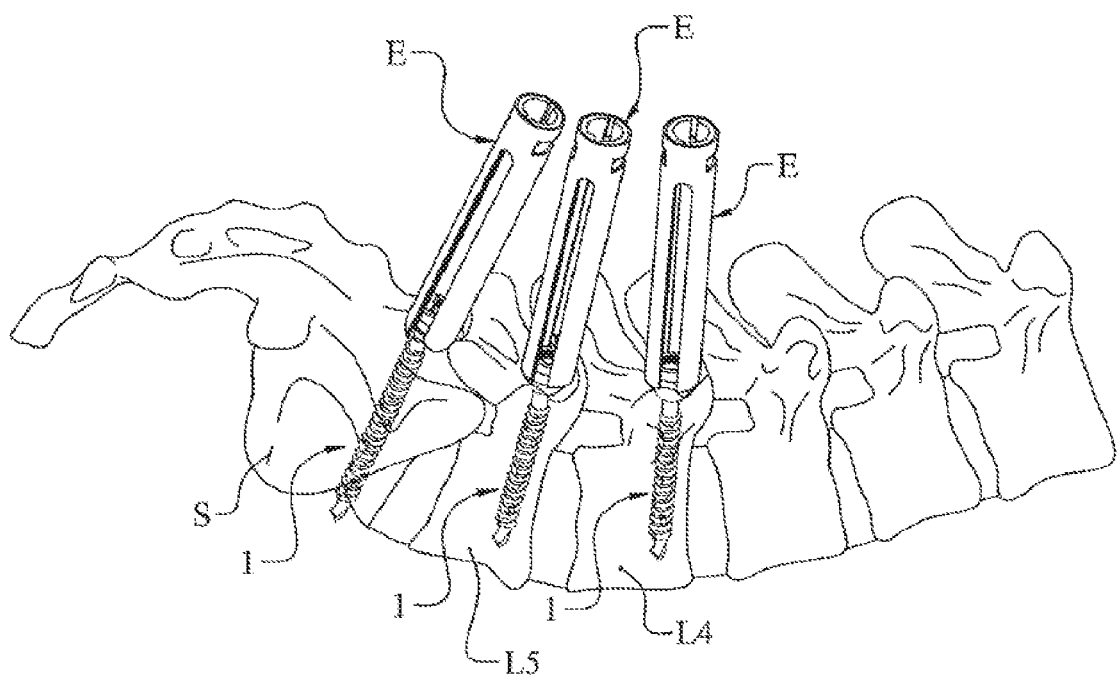
FIG. 23 illustrates a percutaneous surgical technique with multi-level fixation using self-drilling, self-tapping cannulated pedicle screws of the present disclosure with a first screw inserted into the sacrum, a second screw inserted into the next adjacent lumbar vertebrae L5, and a third screw inserted into the next adjacent lumbar vertebrae L4.

FIG. 23 of the present disclosure illustrates a percutaneous minimally invasive surgical (MIS) procedure for multilevel fixation with fully cannulated, self-drilling and self-tapping screws 1 of the present disclosure placed bicortically in sacrum S and unicortically in vertebrae L4 and L5. Alternatively, because only unicortical fixation is desired in the vertebrae, conventional blunt tipped MIS screws may be used. It is understood that because the tapping step of traditional pedicle screw placement has been eliminated by the screw 1 of the present disclosure, less time is required for screw placement and greater surgical productivity is achieved.

Those skilled in the art will appreciated that the internal threads formed in the bone structure by screw 1 of the present disclosure of bone perfectly match external threads of screw 1 thus maximizing the pullout strength of the screw. It will be recognized by those skilled in the art there when a separate tapping step is employed, there may be some degree of mismatch between threads created by a tap and actual threads generated by screw placement owing to the soft bone material. It is also understood that different self-drilling screw types and combinations could be substituted for those depicted in FIG. 23 including fenestrated fully cannulated and blind end cannulated necessitating modified insertion technique are detailed in my U.S. patent application Ser. No. 14/148,270 to prevent bone core from occluding fenestrations.

As previously noted, a screw of the present disclosure may be non-cannulated or may be blind end cannulated having the self-drilling, self-tapping features of a screw 1. Such non-cannulated or blind end cannulated screws in accordance with this disclosure will have drill point similar to that shown in FIGS. 2-11 except the no cannula extends through the distal tip of the screw, and thus eliminate the need for a tapping step now commonly practiced in open pedicle screw placement procedures.

Screws of the present disclosure would also have application in a wide array of procedures. For example, while certain prior art self-drilling screws having a sharp Gimlet point are used in craniofacial and small cervical applications, such prior screws must be impacted into the bone for initial penetration of the drill tip into the bone. Then, significant torque and axial thrust must be allied to the screw to penetrate the proximal cortical bone. While such screws may be appropriate for unicortical applications, bicortical purchase offers greater pullout strength but presents several technical challenges. Specifically, pilot holes must be drilled through the distal cortical bone, which is typically not directly visualized by the surgeon. For that reason, oftentimes unicortical purchase of such screws is accepted. However, because the length of the screw can usually readily be determined in advance through fluoroscopic viewing of the bone structure into which they are to be installed, screws of the present disclosure can now be used for bicortical purchase without the need for such pilot holes. It will be further appreciated by those skilled in the art that the self-drilling, self-tapping bone screws of the present disclosure offer significant advantages in many areas of orthopedic surgery including foot, ankle, and hand fractures because in many instances pilot holes would not be required (or would be very shallow) or the cortical bone need only be scored to initiate penetration by the screw. Still further, those skilled in the art would recognize that fixation strength would be greatly enhanced in applications in small bone because the threads in the bone is formed by a single pass of the self-drilling, self-tapping screw of the present disclosure that achieves bicortical purchase.

It will be appreciated that the methods described by the following method claims specify instructing a surgeon or the like to perform a series of steps. In the method claims, those steps are listed one after the other, but those skilled in the art will recognize that the order of the steps may not be important, but rather that the listed steps be performed.

As various changes could be made in the above constructions without departing from the broad scope of the invention, it is intended that all matter contained in the above description or shown in the accompanying drawings shall be interpreted as illustrative and not in a limiting sense.

The invention claimed is:

1. A method of installing a self-drilling, self-tapping bone screw into a bone structure, said screw having a distal end and a proximal end, a self-drilling and self-tapping drill tip at the distal end of said screw, a head at the proximal end of said screw, and a shank extending from said head toward the distal end of the screw, said screw having a cannula extending lengthwise of the screw from said head through said head and through said drill tip at the distal end of the screw, said screw having bone threads on said shank extending along at least a portion of its length, said bone structure having a proximal and a distal cortical bone layer with a cancellous bone region therebetween, each of said cortical bone layers having a respective thickness, said drill tip having a generally cylindric drill tip body extending between the drill tip and the distal end of said shank and being free of threads, the drill tip and the drill tip body have a length, the length of the drill tip and the drill tip body being equal to or greater than the thickness of said proximal cortical bone layer, one of said threads at the distal end of said shank constituting a lead thread configured to tap internal threads in said bone structure as said screw is installed in said bone structure, said method comprising the following steps:
   a. installing a guide wire into a proximal area of said bone structure to establish a desired location for insertion of the screw;
   b. passing said screw along said guide wire until the tip of the screw is in contact with said bone structure at said desired location for the insertion of the screw;
   c. rotatably driving said screw such that the tip of the screw begins to penetrate said proximal cortical bone layer and removing the guide wire; and
   d. rotatably driving said screw into said bone structure with said drill tip self-drilling through said proximal cortical bone layer before said lead thread has formed threads in said proximal cortical bone layer.

2. The method of claim 1 further comprising driving said screw through said cancellous bone and into the distal cortical bone layer so that said lead thread forms threads in said distal cortical bone layer thereby to achieve bicortical purchase of said screw in said bone structure.

3. The method of claim 1 wherein said bone structure is the human sacrum having an avascular space on the anterior of the sacrum, and wherein the method further comprises the step of rotatably driving said screw through said distal cortical bone layer until the end of said drill tip extends into said avascular space and until said lead thread has formed at least some threads in said distal cortical bone layer thereby to achieve bicortical purchase of said screw in said sacrum bone structure.

4. A method of installing a self-drilling, self-tapping bone screw into a bone structure, said screw having a distal end and a proximal end, a self-drilling and self-tapping drill tip at the distal end of said screw, a head at the proximal end of said screw, and a shank extending from said head toward the distal end of the screw, said screw having bone threads on said shank extending along at least a portion of its length, said bone structure having a proximal and a distal cortical bone layer with a cancellous bone region therebetween, each of said cortical bone layers having a respective thickness, said drill tip having a drill tip body extending between the drill tip and the distal end of said shank and being free of threads where the drill tip and the drill tip body have a length, the overall length of the drill tip and the drill tip body is equal to or greater than the thickness of said proximal cortical bone layer, one of said threads at the distal end of said shank constituting a lead thread configured to tap internal threads in said bone structure as said screw is installed in said bone structure, said method comprising the following step:
   driving said screw into said bone structure by rotating said screw with said drill tip self-drilling through said proximal cortical bone layer before said lead thread begins to form threads in said proximal cortical bone layer so as to avoid stripping of the threads formed in said proximal cortical bone structure whereby said drill tip driving through said proximal cortical bone layer before said lead thread begins to form threads prevents the threads being formed from being stripped because the drill tip advances through the cancellous bone rather than being impeded by the proximal cortical bone structure during formation of the threads.

5. The method of claim 4 wherein said method further comprises driving said screw through said cancellous bone region and into said distal cortical bone layer so that said lead thread forms threads in said cancellous bone region and in said distal cortical bone layer without stripping of the threads formed in said proximal cortical bone structure, in said cancellous bone region, and in said distal cortical bone layer thereby to achieve bicortical purchase of said screw in said bone structure.

6. The method of claim 4 wherein said bone structure is the human sacrum having an avascular space on the anterior of the sacrum, and wherein the method further comprises rotatably driving said self-drilling screw through said distal cortical bone layer until at least a portion of said drill tip extends into said avascular space and until said lead thread has formed one or more threads in said distal cortical bone layer thereby to achieve bicortical purchase of said screw in the sacrum.

7. A method of installing a self-drilling, self-tapping bone screw into a bone structure, said screw having a distal end and a proximal end, a self-drilling and self-tapping drill tip at the distal end of said screw, a head at the proximal end of said screw, and a shank extending from said head toward the distal end of the screw, said screw having a longitudinal axis extending lengthwise of the screw from said head through said drill tip at the distal end of the screw, said screw having bone threads on said shank extending along at least a portion of its length, said bone structure having a proximal and a distal cortical bone layer with a cancellous bone region therebetween with each of said cortical bone layers having a respective thickness, said drill tip having a drill tip body extending between the drill tip and the distal end of said shank and being free of threads where the drill tip and the drill tip body have a length, the overall length of the drill tip and the drill tip body is equal to or greater than the thickness of said proximal cortical bone layer, one of said threads at the distal end of said shank constituting a lead thread configured to tap internal threads in said bone structure as said screw is rotatably installed in said bone structure, said method comprising the following steps:
   a. establishing an insertion point on the bone structure for the insertion of said screw and establishing a desired line of insertion for said screw;
   b. positioning the drill tip of said screw on said insertion point and orienting said screw such that the longitudinal axis of said screw is aligned with said desired line of insertion; and
   c. driving said screw into said bone structure by rotating said screw with said drill tip self-drilling into said proximal cortical bone layer and with said lead thread only forming internal threads in said proximal cortical bone layer after said drill tip has penetrated through said proximal cortical bone layer thereby to avoid stripping of the threads formed in said proximal bone layer.

8. The method of claim 7 wherein said method further comprises rotatably driving said screw so that said screw self-drills and self-taps threads in said proximal cortical bone layer and in said cancellous bone region, and self-drill and self-taps at least some threads in said distal cortical bone layer thereby to achieve bicortical purchase of said screw in said bone structure.

9. The method of claim 8 wherein said bone structure is a human sacrum that has an avascular space on the anterior of the sacrum, and wherein the method further comprises continuing to rotatably drive said screw through said distal cortical bone layer of the sacrum until the drill tip extends at least partially into said avascular space.

\* \* \* \* \*